Figure 1:
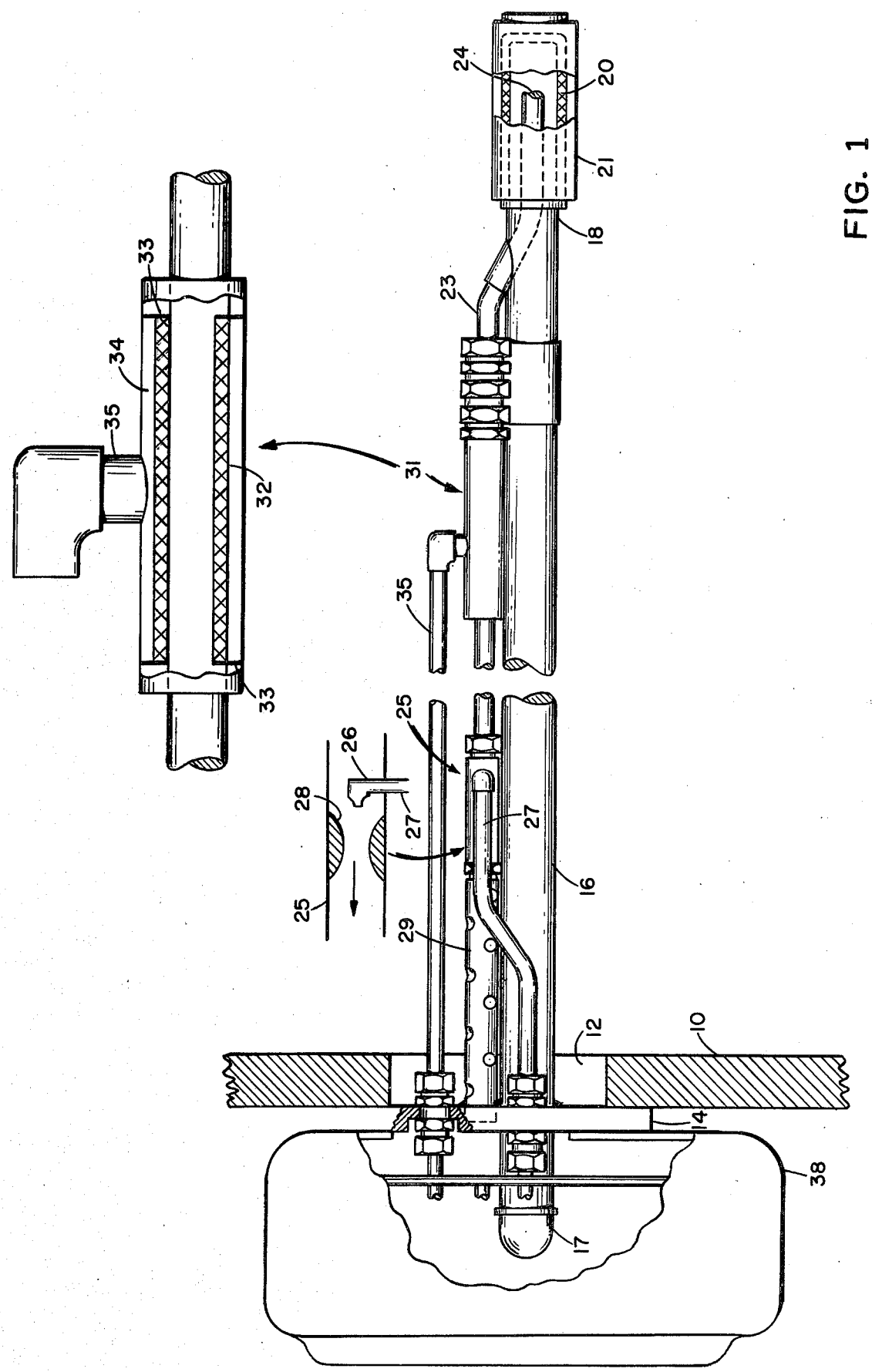

United States Patent [19]

Laird et al.

[11] 4,161,883
[45] Jul. 24, 1979

[54] CONDITIONING ASSEMBLY FOR CONTINUOUS STACK MONITORING

[75] Inventors: James C. Laird, Maxwelton; Robert L. Tomlin, Lewisburg, both of W. Va.

[73] Assignee: The Bendix Corporation, Southfield, Mich.

[21] Appl. No.: 908,868

[22] Filed: May 23, 1978

[51] Int. Cl.² ............................................. G01N 1/24
[52] U.S. Cl. ............................................. 73/421.5 A
[58] Field of Search ..................... 73/421.5 R, 421.5 A

[56] References Cited

U.S. PATENT DOCUMENTS

| | | | |
|---|---|---|---|
| 3,289,481 | 12/1966 | Barnes | 73/421.5 A |
| 3,705,478 | 12/1972 | Vaneldik | 73/421.5 A |

FOREIGN PATENT DOCUMENTS 2603948  9/1976  Fed. Rep. of Germany ..... 73/421.5 A

Primary Examiner—S. Clement Swisher
Attorney, Agent, or Firm—Bruce L. Lamb; William G. Christoforo

[57] ABSTRACT

A probe for obtaining particulate-free samples of gas from a smoke stack for a power plant or other industrial installation. The probe comprises a coarse filter, with means for periodic cleaning by blowback, protecting the inlet to an inertial filter. A high velocity flow of coarsely filtered stack gas is established through the inertial filter. Sample gas is withdrawn from the inertial filter at a low rate in a direction orthogonal to the gas stream through the inertial filter so as not to disturb particles in the inertial filter stream. The invention eliminates the necessity for frequent maintenance of stack mounted filters or other stack mounted components.

6 Claims, 2 Drawing Figures

CONDITIONING ASSEMBLY FOR CONTINUOUS STACK MONITORING

The present invention relates to stack gas sampling systems. More particularly, it relates to a combination blowback probe and sample conditioning assembly for continuous monitoring of stack gases.

Recent stringent regulations adopted for the purpose of improving air quality by control of the emission of pollutants from stationary sources such as generating plants and factories have created an urgent necessity for effective stack gas monitoring equipment. These gases may be analyzed directly in the stack by optical methods involving photometry or spectrometry. Such methods, however, lack reliability since their sensitivities are degraded by the particulate matter in the stack stream and by accumulations of dirt on windows, lenses or reflectors. Another method of analysis involves extracting a particulate-free sample from the stack stream and conveying it to remotely located instrumentation which may be of the optical, wet chemical or chromatographic type. Because of the conveniences afforded by locating the analytical equipment remotely from the stack sampling point, it is the latter method which is of interest herein.

The major problems associated with the extractive method are the elimination of particulate matter from the sample, assuring that the sample line remains free from obstruction due to condensation or corrosion and assuring that the sample undergoes no change in transit from the stack to the analyzer. Elimination of particulate matter is accomplished by filtering the gases from the solid matter in the stack stream. Maintaining the sample lines free and preserving the original nature of the sample is accomplished either by heat tracing the sample line to keep all constituents of the sample above their dew points throughout their transit of the line or, preferably, by conditioning the sample at the stack prior to its injection into the line to remove corrosive aerosols and water vapor therefrom. Of the foregoing solutions the one which has proven most difficult to implement in a satisfactory manner has been the filtration of gases from the solids in the stack stream and it is towards improvement in this filtration that the present invention is directed.

In the extractive method a probe is projected through the stack wall a suitable distance into the stack stream. The inlet to the probe through which the sample is withdrawn is fitted with a porous filter. Past practice has been to use a filter capable of screening out particles of greater than 5-30$\mu$. size. Such filters clog rapidly in the severe environment to which they are exposed necessitating frequent replacement or cleaning. Stack probes are often mounted high above the ground, making filter replacement hazardous and time consuming. Some relief in replacement and cleaning effort is gained by providing automatic periodic blowback through the filter to dislodge entrapped particles. However, blowback does not provide effective long term purging in filters below about 100$\mu$. porosity, so periodic replacement of the filter remains necessary.

As an alternative to fitting fine grain filters to the sampling probe a reflux probe has been developed. The reflux probe employs a pump mounted on the stack adjacent the probe breaching to draw a flow from the stack stream into a chamber, circulate the flow through the pump and discharge substantially all of the flow back into the chamber in a direction counter to the inlet flow. A small sample of the circulating flow is bled off for supply to the analyzer. By refluxing the flow in this manner very little momentum is imparted to the solids in the stack stream in the direction of the pump inlet and the extracted sample is substantially free of particulate matter. Although these means go far toward eliminating probe clogging, the stack mounted pump must be heated in certain applications and is often a source of failure due to corrosion and mechanical wear.

It is an object of the present invention to provide a stack gas sampling probe which is capable of providing gas samples which are substantially free of particulate matter.

It is another object of the present invention to provide a probe for a stack gas sampling system which is self-cleaning and capable of functioning for an extended period of time without requiring routine maintenance.

It is a further object of the invention to provide a stack gas sampling probe which operates at the temperature of the stack stream, which does not employ stack mounted components vulnerable to failure because of wear or corrosion and which requires only simple interconnections between the probe and a remotely located monitoring station.

Other objects and advantages of the invention will be appreciated as the same becomes better understood through study of the following detailed description in connection with the accompanying drawings.

Briefly, the invention comprises a blowback pipe secured at one end to a flange mounted on the exterior of the stack wall with the pipe projecting into the stack. The end of the pipe within the stack is covered with a sintered metal cap having a porosity in the range of 100–500$\mu$. A collector tube extends parallel to the blowback pipe within the stack. An air operated ejector is fitted to the end of the collector tube adjacent the stack mounting flange. The other end of the collector tube penetrates the blowback pipe near the porous cap and extends forwardly into the cap. An inertial filter through which sample gas is extracted is located medially within the collector tube. The inertial filter comprises an open ended, hollow sintered metal cylinder of smaller external diameter than the internal diameter of the collector tube. The cylinder is supported in the tube by end baffles which cause the flow in the collector tube to pass axially through the cylinder and which create a confined space surrounding the cylinder. A sample line is tapped into this space to carry the gases therein to conditioning means mounted on the flange exteriorly of the stack. The ejector is operated so as to establish a high velocity flow through the tube thereby imparting substantial momentum to any particles in the tube stream. The sample gases are drawn off at a low flow rate in a direction orthogonal to the direction of momentum of particles in the tube stream, thus avoiding diversion of particulate matter into the sample line.

Figure 2:
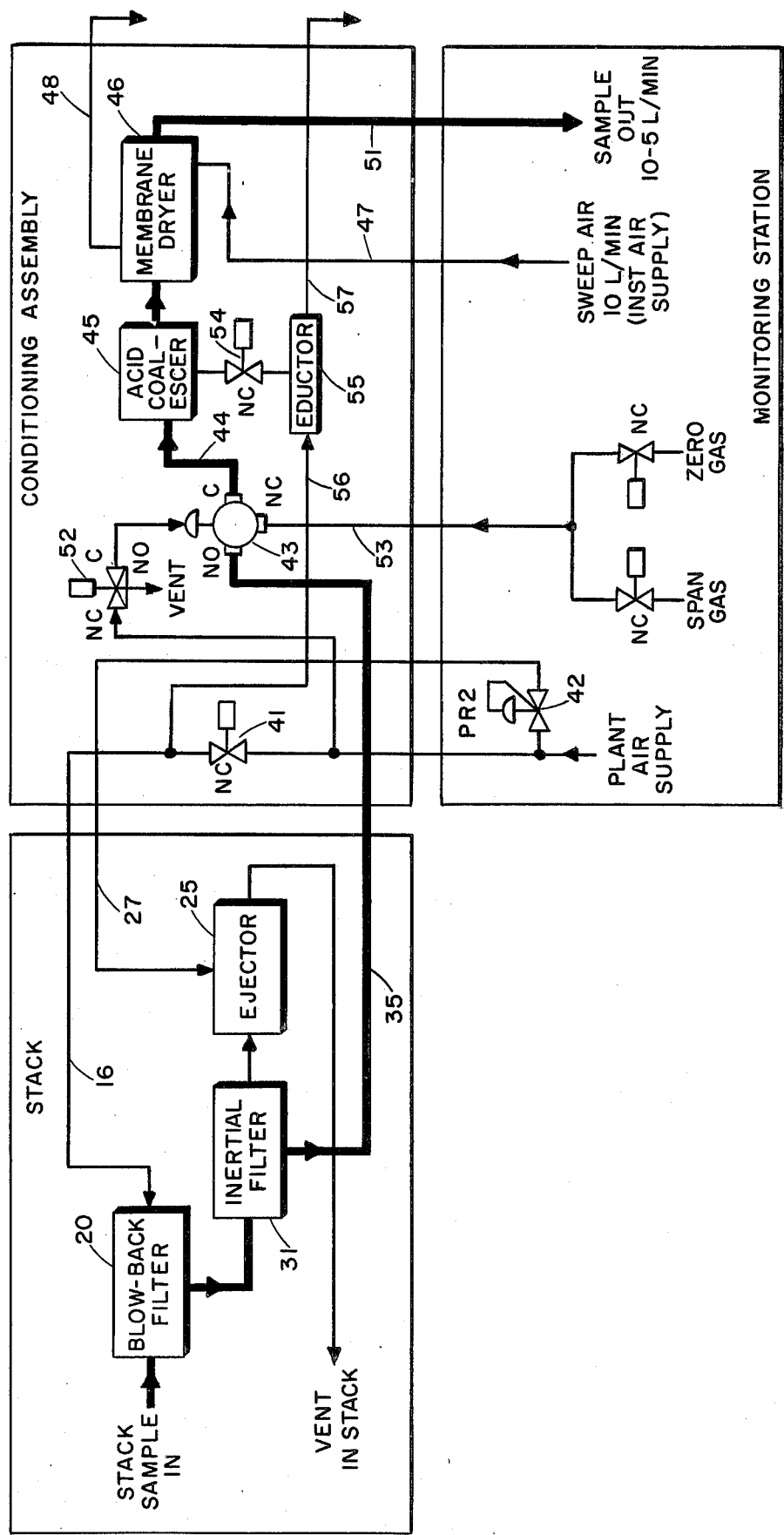

In the drawings:

FIG. 1 is an elevation view of the probe of the invention with portions thereof broken away to show interior construction; and FIG. 2 is a schematic diagram showing the probe, stack mounted components of the sample gas conditioning apparatus and interconnections to the monitoring station.

Referring to FIG. 1, a stack wall 10 is shown with a breach 12 therein which is covered by a probe mounting flange 14. A blowback pipe 16 secured to flange 14 extends through the flange and breach 12 to the interior of the stack. The exterior end 17 of pipe 16 is connected to a source of compressed air through a solenoid valve (not shown in FIG. 1) which periodically admits blasts of cleaning air to the pipe. The interior end 18 of pipe 16 is closed by a hollow, sintered metal filter cap 20. Cap 20 is selected to have a porosity not lower than $100\mu$. and preferably not higher than $500\mu$. A filter cap with a porosity rating of less than $100\mu$. cannot be reliably maintained clean by periodic air blasts. An open ended cylindrical metal shield 21 is supported by pipe 16 spaced from and surrounding filter cap 20 to protect the latter from direct impingement by high velocity particles carried by the stack stream.

A collector tube 23 is sealed into an opening in pipe 16 near the interior end 18 thereof and extends forwardly to present an open end 24 within the filter cap 20. An ejector 25 supported by flange 14 is fitted to the end of tube 23 adjacent the stack wall. As seen in the inset view ejector 25 comprises a jet 26, which is furnished with a continuous supply of compressed air by pipe 27, and a nozzle 28. The air stream from jet 26 is directed into the throat of nozzle 28 thereby inducing a vacuum upstream of the nozzle throat and a consequent high velocity flow which commences at the open end 24 of tube 23, passes through the tube and exits downstream of the nozzle throat. The exit end of nozzle 28 is connected to a perforated exhaust tube 29 which discharges the ejector flow into the stack stream.

Sample gas is extracted through an inertial filter 31 located medially of the length of tube 23. As seen in the inset view, filter 31 comprises an open ended cylindrical sintered metal tube 32 having a smaller external diameter than the internal diameter of tube 23. Cylinder 32 is supported spaced from the inner wall of tube 23 by open centered circular end baffles 33 which create a confined space 34 surrounding the cylinder. A sample line 35 is tapped into tube 23 so as to communicate with the space 34 surrounding cylinder 32. Cylinder 32 preferably has a nominal porosity of $2\mu$. and ejector 25 is operated to provide a flow velocity of at least 80 ft./sec. therethrough. Cylinder 32 may suitably have an internal diameter of 0.25 in., resulting in a volume flow of approximately 1.6 cu. ft./m n. or 46.3 l./min. at a flow velocity of 80 ft./sec. A moderate vacuum is applied to line 35 by a sampling pump (not shown) located at the remote monitoring station to extract sample gas from the space 34 The flow of sample gas in line 35 is at a low rate of from about 0.1 l./min. to not more than 5 l./min. Such a low sample gas flow has a negligible effect on the momentum of particles entrained in the stream flowing through tube 23, hence the gas sample is substantially free of all particulate matter. Moreover there is little tendency for particles to enter and become entrapped in the pores of cylinder 32 and any particles adhering momentarily to the inner surface of the cylinder are scoured away by the high velocity particles of the passing stream.

The gas sample in line 35 passes through flange 14 into a gas conditioning assembly contained within housing 38 secured to flange 14 exteriorly of the stack. The gas conditioning assembly removes acid mists and water vapor present in the sample gas prior to its transmission to the remote monitoring station, thereby alleviating problems with freezing and corrosion of the sample transmission line. Suitable conditioning apparatus has been described in the article "Continuous Stack Monitoring" by R. L. Chapman published in Environmental Science and Technology, June 1974 pp. 520–525. The conditioning apparatus employed with the present invention is shown schematically in FIG. 2, to which reference will now be made.

Blowback pipe 16 is connected through an electrically operated solenoid valve 41 to the plant air supply. Valve 41 is periodically briefly opened by an automatic timer (not shown) to admit a blast of air to pipe 16 for purging the coarse particulate filter 20. A continuous flow of air is furnished to ejector 25 through pipe 27 which is connected to a pressure regulator 42 supplied with unregulated air from the plant air supply. Regulator 42 is best located at the monitoring station for convenience of adjustment. The sample gas in line 35 containing acid mist and water vapor is conducted a short distance to a three-way valve 43 in the conditioning assembly mounted at the stack breach. The sample gas in line 35 normally passes through valve 43 to common line 44 and into an acid mist coalescer 45. Coalescer 45 separates acid mists and a certain amount of water vapor from the sample gas by condensation. From the coalescer the sample gas passes into a membrane dryer 46 where the water vapor remaining in the sample is removed. Dryer 46 comprises a manifold of membrane tubing through which the sample gas flows and which is permeable to water vapor. A current of dry purging air supplied by line 47 surrounds the manifold and carries away to discharge line 48 water vapor permeating through the membrane tubing. The sample gas, now freed of acid mist and water vapor, exits dryer 46 and enters line 51 for transmission to the monitoring station.

Valve 43 is pneumatically operated under the control of a solenoid operated control valve 52. Actuation of valve 52 applies air pressure from the plant air supply to valve 43 causing the latter to switch common line 44 from connection with sample gas line 35 to test gas line 53. Either zero gas, to which the analytical apparatus at the monitoring station should not respond, or known concentrations of span gas, to which the analytical apparatus is sensitive, may be introduced in line 53 for purposes of instrument calibration and to test the integrity of the conditioning assembly and the sample transmission line.

The acid mists and water vapor condensed from the sample gas by coalescer 45 are collected in a sump formed as an integral part of the coalescer. This condensate is periodically drained from the coalescer sump by a solenoid valve 54 which is operated simultaneously with valve 41 to connect the sump with the vacuum port of an air operated eductor 55. When valve 41 is opened to admit air to pipe 16 for purging filter 20, air is admitted to line 56 which flows through ejector 55 inducing a vacuum at the port thereof connected to the outlet of valve 54, then also open. The condensate collected in the sump of coalescer 45 as extracted and ejected along with the exhaust air from ejector 55 into a discharge line 57.

Obviously modifications and variations of the present invention are possible in the light of the foregoing teachings without departing from the spirit and scope of the appended claims.

The invention claimed is:

1. A probe for collecting samples of industrial gas, comprising
   a first tubular conduit having at least one open end;
   means supporting said first conduit within a stack containing a stream of industrial gases with the open end of said first conduit extending into said stream;

a second tubular conduit open at both ends, said second conduit penetrating said first conduit so as to intercept at one end of said second conduit flow within said first conduit;

an inertial filter interposed in said second conduit medially of the ends thereof, said inertial filter including a cylinder of porous material open at both ends connected said second conduit to receive and conduct axially through said cylinder gases flowing in said second conduit, said inertial filter further including a covering wall of gas impervious material surrounding the exterior of said cylinder in spaced relationship thereto so as to create a confined space surrounding the exterior of said cylinder;

a second filter of gas pervious material enclosing said open end of said first conduit, the porosity of said second filter being not less than about 100 microns;

means for establishing a relatively high velocity flow of gases from said stack through said second filter, said second conduit and said inertial filter;

means communicating with said confined space of said inertial filter for extracting sample gas at a relatively low velocity flow, the direction of said sample gas flow being substantially orthogonal to the direction of flow of stack gas through said inertial filter; and means for periodically applying a blast of pressurized fluid to said first conduit for cleansing said second filter of material trapped therein.

2. A probe for obtaining continuous samples of particulate free gas from a stack containing a flow of industrial gases, comprising a first tubular member;

means mounting said first tubular member to a stack containing a stream of industrial gas so that said first tubular member extends from the exterior of said stack to the interior thereof in a direction transverse to the stream of gases in said stack;

a filter cap of porous material enclosing the end of said first tubular member within said stack stream;

a second tubular member having one end penetrating said first tubular member adjacent said filter cap and another end terminating within said stack;

means for establishing a relatively high velocity flow of gases in said second tubular member, said gases being drawn through said filter cap and ejected from said second tubular member at the terminal end thereof within said stack;

a hollow cylinder of porous material inserted in said second tubular member and positioned so that the gas stream in said second tubular member flows axially through said cylinder;

baffle means extending between the ends of said cylinder and the interior wall of said second tubular member so as to create a confined space surrounding the exterior of said cylinder;

a sample gas conduit communicating with said confined space surrounding said cylinder and extending to the exterior of said stack; and means for establishing a relatively low velocity flow of sample gases in said conduit, said sample gases being drawn from said confined space surrounding said cylinder and conducted by said sample gas line to the exterior of said stack.

3. A probe as claimed in claim 2, with additionally, means for periodically injecting a blast of air from the exterior of said stack into said first tubular member for dislodging particulate matter trapped by said filter cap.

4. A probe as claimed in claim 3 wherein said means for establishing a relatively high velocity of flow of gases in said second tubular member comprises an air operated ejector including a nozzle section;

a vacuum section coupled to said nozzle section;

means for injecting a continuous stream of air into said nozzle section whereby a vacuum is induced in said vacuum section; and means for coupling said vacuum section to said terminating end of said second tubular member.

5. A probe as claimed in claim 4 wherein said ejector establishes a flow of gases in said second tubular member of at least about eighty feet per second.

6. A probe as claimed in claim 4 wherein said filter cap is constructed of material permitting particles of about one hundred microns and smaller to pass therethrough.

* * * * *